United States Patent

Friedrich et al.

[11] Patent Number: 5,856,543
[45] Date of Patent: Jan. 5, 1999

[54] SILANES COMPRISING BRANCHED ALKYL CHAINS

[75] Inventors: Holger Friedrich, Bad Dürkheim; Harald Keller, Ludwigshafen; Bernd Leutner, Frankenthal, all of Germany

[73] Assignee: BASF Aktiengesellschaft, Ludwigshafen, Germany

[21] Appl. No.: 629,843

[22] Filed: Apr. 10, 1996

[30] Foreign Application Priority Data

Apr. 15, 1996 [DE] Germany ............ 195 14 258.6

[51] Int. Cl.⁶ ................ C07F 7/08; C07F 7/10; C07F 7/12
[52] U.S. Cl. .......... 556/413; 556/465; 556/442; 556/482
[58] Field of Search .......... 556/465, 413, 556/442, 482

[56] References Cited

U.S. PATENT DOCUMENTS

| | | | |
|---|---|---|---|
| 2,510,853 | 6/1950 | Barry et al. | 556/465 |
| 3,825,607 | 7/1974 | Descoins et al. | 556/465 X |
| 4,695,643 | 9/1987 | Oertle et al. | 556/442 X |
| 4,857,613 | 8/1989 | Zolk et al. | 526/128 |
| 5,710,301 | 1/1998 | Fujiki et al. | 556/465 X |

FOREIGN PATENT DOCUMENTS

| | | |
|---|---|---|
| 14523 | 8/1980 | European Pat. Off. |
| 23425 | 2/1981 | European Pat. Off. |
| 45975 | 2/1982 | European Pat. Off. |
| 195497 | 9/1986 | European Pat. Off. |
| 250229 | 12/1987 | European Pat. Off. |
| 252372 | 1/1988 | European Pat. Off. |
| 273867 | 7/1988 | European Pat. Off. |
| 535691 | 4/1993 | European Pat. Off. |
| 2851456 | 6/1980 | Germany |
| 93/24539 | 12/1993 | WIPO |

OTHER PUBLICATIONS

Schildknecht, Calvin E., "Vinyl and Related Polymers", New York 1952, pp. 534–571.
Marciniec, B., "The Reactivity in . . . Bonds", Comp. Handbook on Hydrosilylation, Oxford–NY (1992), 99–107.
Unger, K.K., Porous Silica . . . , J. Chromatography Library, vol. 16, 1979, pp. 83–124.
Noll, W., "Chemie und Technologie der Silicone", Verlag Chemie GmbH (1960), p. 59.
Meth. der Organ, Chemie, Houbenn–Weyl, vol. XIII/5, (1980), p. 31–51, 173–177, 190–199, 229–232.
Witucki, G.L., A Silane Primer: . . . ', J. Coat. Tech., 65 (1993) 822, pp. 57–60.
Pluedemann, E.P., "Silane Coupling Agents", Plenum Press, NY (1982), pp. 187–208.

Primary Examiner—Paul F. Shaver
Attorney, Agent, or Firm—John H. Shurtleff

[57] ABSTRACT

Silanes of the general formula I

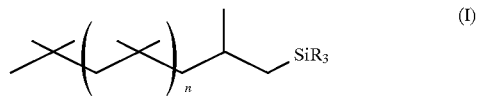

wherein n is an integer of from 1 to 5, at least one of the residues R represents a hydrolyzable residue selected from the group of substituents consisting of halogen, alkoxy, sec. amino and oxycarbonyl hydrogen or oxycarbonyl alkyl, and the other residues represent alkyl, cycloalkyl, aryl or one of the said hydrolyzable residues, a process for their preparation, and their use.

10 Claims, No Drawings

SILANES COMPRISING BRANCHED ALKYL CHAINS

The present invention relates to novel silanes of the general formula I

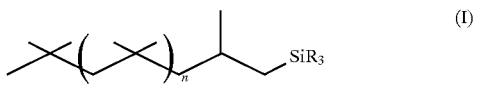

wherein n is an integer of from 1 to 5, at least one of the residues R represents a hydrolyzable residue selected from the group of substituents consisting of halogen, alkoxy, sec. amino and oxycarbonyl hydrogen or oxycarbonyl alkyl, and the other residues represent alkyl, cycloalkyl, aryl or one of the said hydrolyzable residues.

Furthermore, the present invention relates to a process for the preparation of silanes of the formula I, and the use of silanes of the general formula

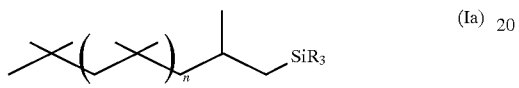

wherein n is an integer of from 0 to 5 and the residues R are defined as in claim 1, for hydrophobizing of porous mineral substrates, for the preparation of chromatographic phases, or coating inorganic pigments, for the preparation of insulating films of electronic devices on the basis of silicane, for coating glasses or as a stereo-modifier in the polymerization of α-olefins.

Silanes comprising long n-alkyl chains and at least one hydrolyzable residue bonded to the silicon atom are used for the hydrophobization of glass (EP-A 535 691) or other inorganic substrates (EP-A 273 867).

German laid-open application 28 51 456 relates to a process for the preparation of organosilicon compounds by using a tubular reactor as defined therein, which is characterized in that the reactor content is circulated at a speed of at least 1,000 cm/min. As an example this reference discloses the reaction of trichlorosilane and diisobutylene leading to 2,4,4-trimethylpentyltrichlorosilane.

EP-A 252 372 relates to the preparation of polyisobutanes carrying silicon groups and having a molecular weight of 500 to 30,000. The obtained silanes exhibit the molecular weight distribution of the polymers used as starting compounds. Such chemically non-uniform products are often undesirable for technical applications. For example, for the generation of monolayers on inorganic substrates only certain silanes having well-defined alkyl chains are suitable in order to generate high quality layers. For other applications, such as the protection of buildings, it is disadvantageous that the fractions of high molecular weight which are present in the functionalized polyisobutenes react significantly slower than the low molecular weight fractions. Apart from that, during the addition to polyisobutene no complete conversion may be achieved resulting in that non-functionalized polyisobutene is present in the final product. This is also not desirable since the possible applications of silylated polyisobutanes are based on the further reaction of the silyl groups. Thus, the starting compounds being present in the product may be detrimental since they do not react.

This also applies to the polyolefins which are reacted with a silylating agent as described in WO 93/24539.

Therefore, it was an object of the present invention to provide chemically uniform silanes comprising long branched alkyl chains.

Thus, the above defined silanes of the formula I and a process for producing the same have been found.

Furthermore, the present invention relates to the use of silanes of formula Ia, as defined above, in various technical fields, in particular for coating inorganic substrates and as a stereo-modifier in the polymerization of α-olefins.

The silanes I according to the invention carry, besides a branched alkyl residue, substituents R at least one of which is hydrolyzable. The term "hydrolyzable residue" denotes residues which react in the presence of water by scission of the bond between the silicon atom and the hydrolyzable residue, whereby a silanol is generated which may react further, for example to a siloxane.

As hydrolyzable residues R the following may be used:

halogens such as fluorine, chlorine and bromine, preferably chlorine and bromine, and especially preferably chlorine, alkoxy, wherein the residues may be linear or branched, preferably $C_1$–$C_{12}$-alkoxy, especially preferably $C_1$–$C_4$-alkoxy, such as methoxy, ethoxy, n-propoxy and n-butoxy, secondary amino residues, such as dialkylamino, arylalkylamino, such as methylphenylamino; and diarylamino, such as diphenylamino; preferably di($C_1$–$C_6$-alkyl)amino, such as dimethylamino, diethylamino and dibutylamino, oxycarbonyl hydrogen and oxycarbonylalkyl, preferably $C_2$–$C_8$-oxycarbonylalkyl, such as oxyacetyl and oxypropionyl.

The further residues R may also represent a hydrolyzable residue. Apart from that, the following substituents which are stable under hydrolysis may be used:

Alkyl, wherein the residues may be linear or branched or cyclic, preferably $C_1$–$C_{12}$-alkyl, especially preferably $C_1$–$C_6$-alkyl, such as methyl, ethyl, n-propyl, iso-propyl, n-butyl, sec.-butyl, tert.-butyl, n-hexyl, cyclopentyl and cyclohexyl, Aryl, preferably $C_6$–$C_{10}$-aryl, especially preferably phenyl, wherein the aryl residue may carry one or more inert substituents such as halogen or alkoxy, respectively.

In particular to be mentioned are the following residues SiR$_3$ trichlorosilyl, chlorodimethoxysilyl, dichloromethoxysilyl, trimethoxysilyl, dichloromethylsilyl, dimethoxymethylsilyl, diethoxymethylsilyl, triethoxysilyl, dimethoxycyclopentylsilyl, tert.-butyldimethoxysilyl, and dimethoxyiso-propylsilyl.

Especially preferred are the following silanes:

Trichloro(2,4,4,6,6-pentamethylheptyl)silane, dichloromethyl(2,4,4,6,6-pentamethylheptyl)silane, dimethoxymethyl(2,4,4,6,6-pentamethylheptyl) silane, dimethoxy(2,4,4,6,6-pentamethylheptyl)iso-propylsilane, chlorodimethyl(2,4,4,6,6-pentamethylheptyl)silane, tert.-butyldimethoxy(2,4,4,6,6-pentamethylheptyl)silane, trichloro(2,4,4,6,6,8,8-heptamethylnonyl) silane, chloro(2,4,4,6,6,8,8-heptamethylnonyl)dimethoxysilane, dichloro(2,4,4,6,6,8,8-heptamethylnonyl)methoxysilane, (2,4,4,6,6,8,8-heptamethylnonyl)trimethoxysilane, dichloro(2,4,4,6,6,8,8-heptamethylnonyl)methylsilane, trichloro(2,4,4,6,6,8,8,10,10-nonamethylundecyl)silane, trimethoxy(2,4,4,6,6,8,8,10,10-nonamethylundecyl) silane, or dimethoxy(2,4,4,6,6-pentamethylheptyl) cyclopentylsilane.

The branched alkyl residue of silane I is derived from an iso-butene oligomer. Such oligomers of formula I serve as starting compounds for the preparation of the silanes I according to the present invention.

(II)

Iso-butene oligomers II, wherein n represents an integer of from 1 to 5 are obtained during the technical polymerization of iso-butene to polyiso-butene (C. E. Schildknecht, Vinyl and Related Polymers, New York 1952, p. 534–571) and may be separated from the polymers by distillation. They may be fractionated, thereby obtaining mixtures of more than 90% by weight, preferably more than 95 wt.-% isomers having the same number of carbon atoms are obtained. Iso-butene oligomers of the mixture comprising double-bonds within the inner parts of the molecules partly react in the same way as the oligomers II during the hydrosilylation and lead to the desired products I. Preferably iso-butene oligomers are reacted, wherein n represents 1, 2 or 3.

For the preparation of the silanes I, first an iso-butene oligomer II, generally in the form of a mixture of different isomers which contains the desired isomer as the main component, with a SiH group carrying silane under addition to the double bond. Optionally, the obtained silane I is further reacted in order to introduce certain substituents at the silicon atom.

The iso-butene oligomer II is reacted with a silane carrying as further substituents besides hydrogen, chlorine, bromine, alkyl and/or aryl residues. All further substituents, as mentioned above, are preferably introduced by means of further reactions. Preferred silanes are trichlorosilane, methyldichlorosilane and dimethylchlorosilane.

Hydrosilylations are known from "Comprehensive Handbook on Hydrosilylation", B. Marciniec, Oxford-New York. During this reaction, generally an iso-butene oligomer II is reacted with an equimolar amount or an excess of a silane carrying a SiH group.

The reaction is carried out in the presence of commonly known catalysts for hydrosilylation. As such catalysts suitably used are compounds such as platinum, rhodium or ruthenium compounds, preferably platinum compounds, in particular hexachloroplatinic acid and divinylsiloxane-platinum-O-complex. These catalysts may be used in amounts of from $10^{-2}$ to $10^{-6}$ mol per 1 kg mixture of isomers.

The reaction temperature generally ranges from 80° to 160° C. Generally the reaction is carried out at normal pressure, but may be also carried out at reduced pressure or, if highly volatile silanes are used, at a pressure above atmospheric pressure of up to 10 bar. The reaction may be carried out continuously or batchwise.

The starting compounds, the catalyst and optionally a solvent such as toluene, xylene or turpentine substitute are mixed and generally heated at the reaction temperature for 2 to 24 h. In case it is not desired to work under pressure when using low boiling silanes the silanes may be added to the other components which have already been heated to the reaction temperature. The work-up of the reaction mixture is carried out according to known methods, preferably by distillation.

Further substituents may be introduced in the hydrosilylation products described above by substitution of chlorine or bromine substituents by means of methods known as such:

a reaction with hydrogen fluoride or antimony trifluoride leads to fluorine containing silanes I (W. Noll, "Chemie und Technologie der Silicone", VCH Weinheim 1960, p. 59), the reaction with alcohols, trialkyl orthoformiates or alkali metal alcoholates leads to alkoxy substituted silanes I ("Methoden der Organischen Chemie", Houben-Weyl, Vol. XIII/5, "Organosiliciumverbindungen", Stuttgart 1980), the reaction with carboxylic acids or carboxylic acid anhydrides leads to oxycarbonyl substituted silanes I (s. Houben-Weyl, loc.cit.), the reaction with secondary amines or the alkali metal amides thereof leads to amino substituted silanes I (s. Houben-Weyl, loc.cit.), and the reaction with alkyl or cycloalkyl magnesium halides or with lithium or sodium alkanes or lithium or sodium cycloalkanes leads to silanes of the general formula I comprising 1 or 2 alkyl or cycloalkyl groups instead of the chlorine or bromine residues.

Preferably $C_2$–$C_6$-Alkyl or $C_5$–$C_6$-Cycloalkyl compounds are used as the said alkyl or cycloalkyl compounds. More preferably used are ethyl, n-propyl, iso-propyl, n-butyl, sec.butyl, n-hexyl, cyclopentyl or cyclohexyl compounds.

Of course, also the hydrosilylation products as described above may be subjected to more than one of the said further reactions.

The process according to the invention allows the preparation of the silanes I in high yields.

Silanes of the formula Ia, as defined above, due to their residues which are to be reacted to reactive silanole groups due to hydrolyses, are predominantly used in such technical fields, wherein excellent adhesion of the silanes to a substrate is required. Preferably used are the silanes of the formula I according to the invention, since they exhibit excellent adhesion-improving characteristics. More preferably, the following silanes are used:

trichloro(2,4,4,6,6-pentamethylheptysilane,
dichloro(2,4,4,6,6-pentamethylheptyl)methylsilane,
dimethoxy(2,4,4,6,6-pentamethylheptyl)methylsilane,
dimethoxy(2,4,4,6,6-pentamethylheptyl)isopropylsilane,
chlorodimethyl(2,4,4,6,6-pentamethylheptyl)silane,
tert.-butyldimethoxy(2,4,4,6,6-pentamethylheptyl)silane,
dimethoxy(2,4,4,6,6-pentamethylheptyl) cyclopentylsilane
trichloro(2,4,4,6,6,8,8-heptamethylnonyl)silane,
chloro(2,4,4,6,6,8,8-heptamethylnonyl)dimethoxysilane,
dichloro(2,4,4,6,6,8,8-heptamethyl nonyl)methoxysilane,
(2,4,4,6,6,8,8-heptamethylnonyl)trimethoxysilane,
dichloro(2,4,4,6,6,8 8-heptamethylnonyl)methylsilane,
trichloro(2,4,4,6,6,8,8,10,10-nonamethylundecyl)silane, or
trimethoxy(2,4,4,6,6,8,8,10,10-nonamethylundecyl) silane.

These silanes are used in the preparation of agents which improve the hydrophobic characteristics of inorganic materials. In particular, these silanes may be used in combination with other silanes for the impregnation and hydrophobization of porous mineralic substrates, such as natural stone, brickwork, concrete or facing plaster and serve for improving the water repellency and prohibit the intrusion of water and corrosion accelerating salts.

By the use of such silanes the hydrophobic characteristics of the agents may be significantly improved and the resistance of the protective layers may be increased.

The preparation of such hydrophobizing agents is carried out by admixing one or more of these silanes, preferably of the trialkoxysilanes with alkyl-trialkoxysilanes carrying 1 to 6 carbon atoms in the alkyl chain and optionally a solvent such as turpentine substitute or a $C_2$–$C_6$-alcohol.

Generally it is sufficient to add only a small portion (1 to 10 weight-%) of the silanes to said mixture in order to achieve the full hydrophobizing effect. Condensation catalysts such as dibutyltin dilaurate or titanium orthobutylate, which improve the application characteristics of such hydrophobizing agents since they accelerate the reaction of the silanes at the mineralic surfaces, may be added to these mixtures or solutions. Furthermore, it is possible to prepare a cohydrolysate which exhibits similar characteristics compared to the water-free mixture or solution, by introducing water.

Furthermore, the said silanes may be used for preparing chromatographic phases having improved separation characteristics.

General processes and techniques for preparing such phases are described in the following literature and may be applied in an analogous way: Journal of Chromatography Library, Vol. 16: Porous Silica, Its Properties and Use as Support in Column Liquid Chromatography, Unger, Klaus K., Elsevier, Amsterdam 1979.

For example, for the preparation of such phases silica gel may be suspended in toluene and heated to the boiling point under stirring. Triethylamine and one of the compounds according to the invention, in particular the trichlorosilanes and trialkoxysilanes, are added to the suspension.

The silanes may be used for the coating of inorganic pigments and fillers, in particular for those on the basis of silica, whereby the stability of the pigments against atmospheric influences is increased and their surface characteristics, such as hydrophobic characteristics or gloss, are improved. Furthermore, the compatibility of pigments with strong non-polar media may be improved, leading to a better dispersibility of the pigments in non-polar organic media. Particularly useful are the silanes according to the invention when used in order to render fillers compatible with e.g. elastomers and to incorporate the same thereinto. Processes for coating of pigments are known, e.g. from G. Witucki, J. Coat. Technol. 65 (1993) 822, 57 or E. P. Plueddemann, Silane Coupling Agents, Plenum Press, New York 1982.

The silanes may be also used for generating thin insulating films on electronic devices. During this application monomolecular layers are generated on silicon substrates or devices. These monomolecular layers are self-assembling monolayers, which gather their stability from the reaction and formation of covalent bonds derived from the reaction of the compounds according to the invention with the silanole groups being present in the layer of silicon oxide being present on the silicon.

These layers may be generated by different methods. Preferably, they are generated by means of an immersion method or by spraying the substances on the substrate. Generally, 0,5 to 2 g of one or more of the compounds according to the invention, preferably compounds comprising a trichlorosilyl residue, are dissolved in 100 g of an organic solvent, such as ethanol and the part to be coated is subsequently immersed in the solution for several minutes. Then the device is taken out from the immersing bath and rinsed with the solvent, and finally dried. Optionally for drying increased temperatures may be applied. If silanes I comprising trialkoxysilyl groups are used for coating, it is recommended to add a small amount of water (e.g. 5 to 10 g) several hours before the coating process, and to additionally adjust the pH value of the solution to 4,5 to 5,5 by using an acid, preferably acetic acid, whereby alkoxy groups are hydrolysed and silanol groups which are capable to react with the surface of the substrate, are generated.

The silanes may be applied as hydrophobizing coatings of glass, glass having anti-reflex layers and plastics glasses which are coated by $SiO_2$ or $MgF_2$.

Furthermore, the silanes may be used as stereomodifier within the polymerization of α-olefins. Also in this case, preferably used are the silanes of the general formula I according to the invention, more preferably the silanes of formula I comprising as residues R two methoxy groups and one $C_1$–$C_6$-alkyl groups or a $C_5$–$C_6$-cycloalkyl group. Particularly preferably used are silanes of formula I, wherein two of the residues R represent methoxy and one of the residues R represents methyl, iso-propyl, sec.-butyl, tert.-butyl, cyclopentyl or cyclohexyl.

As the starting compounds for the above mentioned polymerization preferably $C_2$–$C_{10}$-α-olefins, such as ethylene, propylene, 1-butene, 1-pentene, 1-hexene, more preferably ethylene, propylene and 1-butene, particularly preferably propylene are used.

The above silanes are used together with catalyst systems of the Ziegler-Natta-type, which are e.g. known from EP-B 14 523, EP-A 23 425, EP-A 45 975, EP-A 195 497, EP-A 250 229, US 4 857 613 and DE-A-19 609 952. These systems are particularly used for the polymerization of α-olefins and comprise compounds of polyvalent titanium, aluminum halides and/or alkyls and electron donating compounds, such as silicon compounds, ether, carboxylic acid esters, ketones and lactones which are used either in combination with the titanium compound or as a cocatalyst.

EXAMPLES

Example 1

Preparation of Trichloro(2,4,4,6,6,8,8-Heptamethylnonyl)Silane 0.1 ml of a 0.1M $H_2PtCl_6$ .$6H_2O$ solution in isopropanol were added to 100 g of a fraction of side-products of the synthesis of polyisobutene comprising about 98 wt.-% compounds having 16 carbon atoms, and the resulting mixture was heated to 120° C. Trichlorosilane (60 g, 0.44 mol in total) were added to the heated olefin and the temperature was maintained at 120° C. for 16 h. Afterwards, the product was distilled.

Yield: 96 g

NMR data $^{13}$C-NMR, δ (ppm)=25.1, 25.4 (2C), 29.5, 29.7, 30.85, 30.90 (4C), 32.7 (3C), 32.8 (1C), 35.7 (1C), 36.5 (1C), 37.8 (1C), 56.0 (1C), 56.4 (1C), 58.3 (1C)

$^{29}$Si-NMR, δ (ppm)=11.8 b. p.=117° C./0.3 mbar elementary analysis: C 53.9% (calc. 53.4), H 9.0% (calc. 9.24), Cl 29.42% (calc. 29.55).

Example 2

Preparation of Chloro(2,4,4,6,6,8,8-Heptamethylnonyl)Dimethoxysilane

A crude product obtained from the reaction of 79 g of a fraction of oligomers with trichlorosilane (52 g, 0.38 mol) according to example 1, with the exception that the reaction time was only 4 h, was freed from excessive trichlorosilane, mixed with 122 g (1.15 mol) trimethyl orthoformiate and refluxed for 8 h. The reaction mixture was distilled. 31 g dichloro(2,4,4,6,6,8,8-heptamethylnonyl)methoxysilane A with a content of 21% chloro(2,4,4,6,6,8,8-heptamethylnonyl)dimethoxysilane B was obtained as the product.

b. p.=95° to 115° C./<1 mbar

NMR data $^{29}$Si-NMR: δ (ppm)=−9.0 ppm (A); −26,6 (B)

Example 3

Preparation of (2,4,4,6,6,8,8-Heptamethylnonyl) Trimethoxysilane 211.5 g (0.588 mol) trichloro(2,4,4,6,6,8,8-heptamethylnonyl)silane prepared according to the procedure of claim 1 were added to 312 g of a 30% solution of sodium methylate in methanol and 1 l tetrahydrofuran (THF). The reaction mixture was further stirred for four hours. After separating precipitated sodium chloride, THF and methanol were distilled off and the product was purified by distillation.

Yield: 181.9 g, 89%

NMR data $^{13}$C-NMR, δ (ppm)=21.1 (1C), 24.9 (1C), 25.9 (1C), 26.9, 29.8, 30.9, 31.0 (4C), 32.8 (1C), 32.9 (1C), 36.5 (1C), 37.9 (1C), 50.7 (3C), 56.6 (1C), 56.9 (1C), 58.4 (1C)

$^{29}$Si-NMR, δ (ppm)=−42.1 b. p.=107° to 110° C./0.08 mbar elementary analysis: C 65.9% (calc. 65.83), H 11.6% (calc. 12.21).

Example 4

Preparation of (2,4,4,6,6,8,8-Heptamethylnonyl) Trimethoxysilane 33.5 g (0.093 mol) trichloro(2,4,4,6,6,8,8-heptamethylnonyl)silane were introduced at 100° C. Unhydrous methanol was introduced into a washing bottle which was connected to the reactor. A stream of argon (10 l/h) was led through the washing bottle into the chlorosilane. Within 6 h 18.8 g (0.59 mol) methanol was introduced into the reactor. The product was freed from highly volatile components.

Yield: 32.2 g, 100%

$^{29}$Si-NMR, δ (ppm)=42.1 ppm

The direct hydrosilylation of the silane used as the starting compound by means of trimethoxysilane in the presence of H$_2$PtCl$_6$ .6H$_2$O at 110° C. over 10 h did not work.

Example 5

Preparation of Trichloro(2,4,4,6,6,8,8,10,10-Nonamethylundecyl)Silane

To 100 g of a fraction containing side-products of the synthesis of polyisobutene comprising at least 97 wt.-% compounds having 20 carbon atoms were added 0.1 ml of a solution of 0.1M H$_2$PtCl$_6$.6H$_2$O in isopropanol, and the mixture was heated to 120° C. Trichlorosilane (60 g, 0.44 mol in total) were added and the temperature was maintained at 120° C. for 16 h. Subsequently, a vacuum distillation was carried out.

Yield: 59 g

NMR data $^{13}$C-NMR, δ (ppm)=25.02 (1C), 25.07 (1C), 29.2, 29.3, 30.7, 30.89, 30.93 (6C), 32.4 (3C), 35.3 (1C), 32.5, 36.2, 37.65, 37.72 (4C), 55.8, 56.7, 58.1, 58.5 (4C)

$^{29}$Si-NMR, δ (ppm)=11.8 b. p.=158° C./0.2 mbar, content (GC): 98.5% elementary analysis: C 58.7 (calc. 57.74), H 9.7% (calc. 9.94), Cl 25.56 (calc. 25.57).

Example 6

Preparation of Dichloro(2,4,4,6,6,8,8-Heptamethylnonyl)Methylsilane

To 100 g of a fraction of side-products from the synthesis of polyisobutene comprising at least 98 wt.-% of compounds having 16 carbon atoms were added 0.1 m of a solution of 0.1M H$_2$PtCl.6 H$_2$O in isopropanol and the mixture was heated to 120° C. Dichloromethylsilane (50 g, 0.44 mol in total) were added to the heated olefin and the temperature was maintained at 120° C. for 3 h. Subsequently vacuum distillation was carried out.

Yield: 104 g $^{29}$Si-NMR data, δ=31.7 ppm b. p.=114° C./0.3 mbar, content (GC): 96% elementary analysis: C 60.1% (calc. 60.15), H 10.4% (calc. 10.69), Cl 20.5% (calc. 20.89).

Example 7

Preparation of Trichloro(2,4,4,6,6-Pentamethylheptyl)Silane

To 100 g of a fraction of side-products from the synthesis of polyisobutane comprising at least 95 wt.-% of compounds having 12 carbon atoms were added 0.1 ml of a solution of a divinyl siloxane-platinum-O-complex in xylene (3 to 3.5% Pt) and the mixture was heated to 120° C. Trichlorosilane (80 g, 0.59 mol in total) was added to the heated olefin and the temperature was maintained at 120° C. for 7 h. Subsequently a vacuum distillation was carried out.

Yield: 97 g $^{29}$Si-NMR data, δ=11.8 ppm b. p.=106° C./0.3 mbar chlorine content: 35.17% (calc. 35.01)

elementary analysis: C 47.4% (calc. 47.44), H 8.4% (calc. 8.30)

Example 8

Preparation of Trimethoxy(2,4,4,6,6,8,8,10,10-Nonamethylundecyl)Silane

To 108 g of a 30% solution of sodium methylate in methanol and 300 ml

THF were added 83.2 g (0.2 mol) trichloro(2,4,4,6,6,8,8,10,10-nonamethylundecyl) silane resulting in a strongly exothermic reaction. After finishing the dropwise addition it was stirred for 30 min and the precipitated sodium chloride was separated. THF and methanol were distilled off and the product was purified by distillation.

Yield: 66 g, 82%

NMR data $^{13}$C-NMR, δ (ppm)=21.2, 24.9 (1C), 25.9 (1C), 29.7, 29.9, 31.1, 31.3, 31.5 (6C), 32.8 (3C), 32.9, 36.5, 38.1, 38.2 (4C), 50.7 (3 C), 57.2, 57.3, 58.6, 59.0 (4C)

$^{29}$Si-NMR, δ (ppm)=−42.1 b. p.=125° to 130° C./0.01 bar elementary analysis: C 68.2% (calc. 68.55), H 12.1 (calc. 12.51)

Example 9

Preparation of Dichloro(2,4,4,6,6-Pentamethylheptyl)Iso-propylsilane 137.8 g trichloro(2,4,4,6,6-pentamethylheptyl)silane, prepared according to example 7, were dissolved in toluene and heated to 100° C. under argon. By means of a dropping funnel were added 220 ml isopropylmagnesium chloride as a 2 molar solution in THF were added to this solution within 1 h. Subsequently the THF was distilled off by means of a column and the reaction mixture was stirred at 100° C. for 20 h. Filtration was carried out for separating the precipitated solid and the product was isolated by vacuum distillation.

Yield: 59.3 g, 42% b. p.=80° C./0.015 mbar $^{29}$Si-NMR data, δ (ppm) =34.7

Example 10

Preparation of Dimethoxy(2,4,4,6,6-Pentamethylheptyl)Iso-propylsilane 64.8 g dichloro(2,4,4,6,6-pentamethylheptyl)isopropylsilane, prepared according to example 9, were dissolved in 250 ml anhydrous THF under argon. Within 30 min 77 g sodium methylate (30.1% in methanol) were added thereto dropwise while rapidly stirring, and the reaction mixture was stirred for 2 h at room temperature. After separating the precipitated sodium-chloride and removing the solvent by means of a rotational evaporator the remainder was distilled in vacuum over a Vigreux-column.

Yield: 54.6 g, 89% b. p.=83° C./0.015 mbar purity (GC) =99.5 Fl-% elementary analysis: C 67.2% (calc. 67.48), H 12.3% (calc. 12.66), Si 9.1% (calc. 9.28)

$^{13}$C-NMR data, δ (ppm)=12.7 (1C), 17.0 (2C), 22.1 (1C), 24.6 (1C), 25.7 (1C), 29.0 (1C), 29.2 (1C), 32.2 (3C), 32.4 (1C), 35.9 (1C), 50.5 (2C), 55.7 (1C), 56.6 (1C)

$^{29}$Si-NMR data, δ(ppm)=−5.2

We claim:

1. Silanes of the formula I

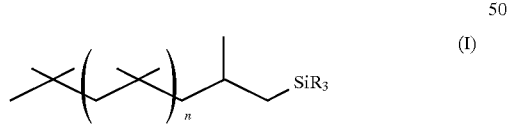

(I)

wherein n is an integer of from 1 to 5, at least one of the residues R represents a hydrolyzable residue selected from the group consisting of halogen, alkoxy, sec amino and oxycarbonyl hydrogen or oycarbonyl alkyl, and the other residues represent alkyl, cycloalkyl, aryl or one of the said hydrolyzable residues.

2. Silanes according to claim 1, wherein at least one of the residues R represents chlorine or $C_1$–$C_4$-alkoxy.

3. Silanes according to claim 1, wherein the group SiR$_3$ is selected from the group consisting of trichlorosilyl, chlorodimethoxysilyl, dichloromethoxysilyl, trimethoxysilyl, dimethynethylsilyl, dimethoxyisopropylsilyl, diethoxymethylsilyl, trietoxysilyl, chlorodimethylsilyl and dichloromethylsilyl.

4. Silanes according to claim 2, wherein the group SiR$_3$ is selected from the group consisting of trichlorosilyl, chlorodimethoxysilyl, dichloromethoxysilyl, trimethoxysilyl, dimethoxymethylsilyl, dimethoxyisopropylsilyl, diethoxymethylsilyl, trietoxysilyl, chlorodimethylsilyl and dichloromethylsilyl.

5. Silanes according to claim 1, wherein n represents 1, 2 or 3.

6. Silanes according to claim 2, wherein n represents 1, 2 or 3.

7. Silanes according to claim 3, wherein n represents 1, 2 or 3.

8. Trichloro(2,4,4,6,6-pentamethylheptyl)silane, dichloromethyl(2,4,4,6,6-pentamethylheptyl)silane, dimethoxymethyl(2,4,4,6,6-pentamethylheptyl)silane, dimethoxy(2,4,4,6,6-pentamethylheptyl)isopropylsilane, chlorodimethyl(2,4,4,6,6-pentamethylheptyl)silane, tert.-butyldimethoxy(2,4,4,6,6-pentamethylheptyl)silane, dimethoxy(2,4,4,6,6-pentamethylheptyl)cyclopentylsilane, trichloro(2,4,4,6,6,8,8-heptamethylnonyl)silane, chloro(2,4,4,6,6,8,8-heptamethylnonyl)dimethoxysilane, dichloro(2,4,4,6,6,8,8-heptamethylnonyl)methoxysilane, (2,4,4,6,6,8,8-heptamethylnonyl)trimethoxysilane, dichloro(2,4,4,6,6,8,8-heptamethylnonyl)methylsilane, trichloro(2,4,4,6,6,8,8,10,10-nonamethylundecyl)silane, or trimethoxy(2,4,4,6,6,8,8,10,10-nonamethylundecyl)silane.

9. Process for the preparation of silanes of the formula I according to claim 1, characterized in that an iso-butene oligomer of the formula II

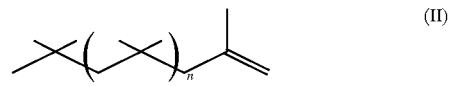

(II)

wherein n is an integer of from 1 to 5 is reacted in the presence of a catalyst for the hydrosilylation with a silane, which carries a SiH group and as further substituents chlorine, bromine, alkyl or aryl under addition to the double-bond, and wherein optionally the chlorine and bromine residues are substituted by fluorine by means of a further reaction with hydrogen fluoride or antimony trifluoride, are substituted by alkoxy groups by means of a further reaction with alcohols, trialkyl orthoformiates or alkali metal alcoholates, are substituted by oxycarbonyl groups by a further reaction with carboxylic acid or carboxylic acid anhydrides, are substituted by sec. amino groups by a reaction with secondary amines or the corresponding alkali metal amides, or are substituted by alkyl or cycloalkyl groups by the reaction with alkyl or cycloalkyl magnesium halides or lithium or sodium alkanes or lithium or sodium cycloalkanes.

10. Process according to claim 9, characterized in that an iso-butene oligomer of the formula II according to claim 9 is reacted with trichlorosilane, methyldichlorosilane or dimethylchlorosilane.

* * * * *